United States Patent [19]

Nonaka et al.

[11] 4,038,146

[45] July 26, 1977

[54] METHOD OF DETERMINATION OF SERUM TRIGLYCERIDES AND REAGENTS

[75] Inventors: Urao Nonaka, Tokyo; Hideto Shibata; Nobuyuki Nakajima, both of Funabashi, all of Japan

[73] Assignee: Latron Laboratories, Inc., Tokyo, Japan

[21] Appl. No.: 531,120

[22] Filed: Dec. 9, 1974

[30] Foreign Application Priority Data

June 7, 1974 Japan .................................. 49-63893

[51] Int. Cl.² ............................................ G01N 31/14
[52] U.S. Cl. ............................................ 195/103.5 R
[58] Field of Search ................................. 195/103.5 R

[56] References Cited

U.S. PATENT DOCUMENTS

| | | | |
|---|---|---|---|
| 3,703,591 | 11/1972 | Bucolo et al. | 195/103.5 R |
| 3,713,986 | 1/1973 | Bergmeyer et al. | 195/103.5 R |
| 3,759,793 | 9/1973 | Stork et al. | 95/103.5 R |

Primary Examiner—Lionel M. Shapiro
Assistant Examiner—C. A. Fan
Attorney, Agent, or Firm—Sughrue, Rothwell, Mion, Zinn & Macpeak

[57] ABSTRACT

A serum sample is added to a reaction liquid obtained by adding an aqueous solution of a mixture of a tetrazolium compound and phenazine methosulfate to an enzyme-coenzyme reagent comprising LPL, GDH and NAD thereby effecting hydrolysis reaction of serum triglycerides and subsequent dehydrogenation reaction of resulting glycerol and the liquid after the reaction is subjected to colorimetry in a visible ray region to determine the triglyceride content of the serum.

2 Claims, 1 Drawing Figure

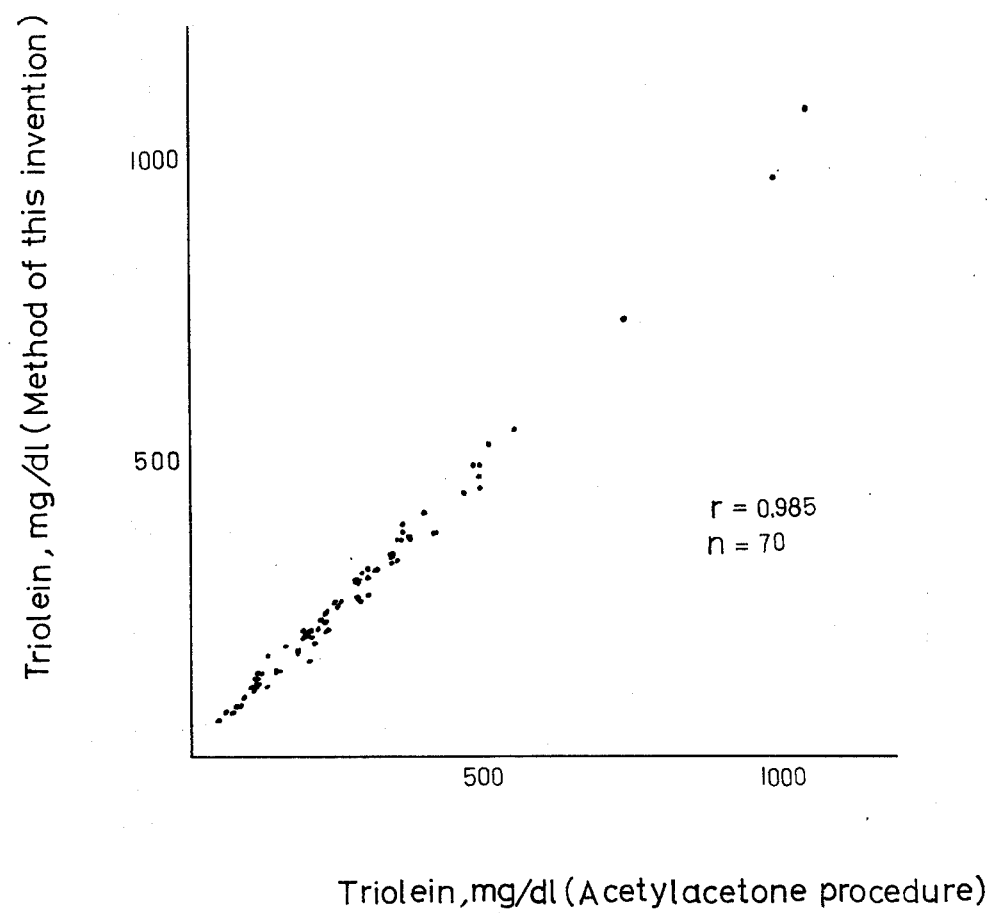

METHOD OF DETERMINATION OF SERUM TRIGLYCERIDES AND REAGENTS

BACKGROUND OF THE INVENTION

The present invention relates to a method of determination of serum triglycerides according to an enzymatic reaction and a reagent used therefor.

The determination of triglycerides is popular as one of lipid tests for hyper-lipoidemia and clinical significance thereof is now being increased. However, the conventional methods of the determination are troublesome in operations and therefore inconvenient for usual tests. For example, in acetylacetone procedure which is most commonly employed at present, triglycerides are first isolated by extraction with an organic solvent, because the neutral fats must not be influenced by phospholipids or saccharides contained in the serum. This procedure is considerably complicated. Then, the triglycerides thus extracted are hydrolyzed with an alkali and glycerol formed by the hydrolysis is oxidized with an oxidizing agent such as sodium metaperiodate, formaldehyde thus formed is condensed with acetylacetone and degree of the color developed is determined by colorimetry. The operation thus comprises several steps. The above acetylacetone procedure is disclosed in, for example, M. J. Fletcher, "A colorimetric method for estimating serum triglycerides" Clinica Chimica Acta 22 (1968) 393–397.

Recently, a method wherein triglycerides are decomposed according to an enzymatic reaction and glycerol thus obtained is determined by increase or decrease of NADH has been attempted. For example, U.S. Pat. Application Ser. No. 98,904 filed on Dec. 16, 1970 discloses a method of analyzing a glycerol ester with a combination of lipase and protease. Further, K. ONOBU, et al. reported the determination of serum triglycerides with lipoprotein lipase-glycerol dehydrogenase in "Study of enzymatic analysis in clinical chemistry " Report 12 [Nihon Yakugaku-Kai 93 nen-Kai (1973)]. According to those methods wherein an enzymatic reaction is utilized, the extraction and adsorption steps necessitated in the acetylacetone method can be omitted. Particularly, the latter hydrolysis of triglycerides with lipoprotein lipase is advantageous in the determination of serum triglycerides, since it is selectively effective for chylomicron and lipoprotein-combinative neutral fats. The dehydrogenation reaction of glycerol is, however, disadvantageous in simplicity and rapidity, because special procedures are required, since the reaction equilibrium is inclined into the NAD formation and a wave length in ultraviolet region is used for the NADH determination. For example, in the enzymatic analysis of K. ONOBU, et al., the enzymatic dehydrogenation reaction equilibrium of glycerol with GDH is inclined into the NAD formation and, therefore, dihydroxyacetone formed by the reaction must be removed from the reaction mixture for advancing the reaction. The dehydrogenation reaction is carried out by adding hydrazine to the reaction mixture to convert dihydroxyacetone into hydrazone. Thus, at present, the determination of triglycerides according to the enzymatic reaction comprises two steps. In addition, in the determination of the resulting NADH at a wave length of 340nm, bilirubin present in the blood has influence on the absorption at the wave length of 340nm and, therefore, a serum blank is indispensable for correcting the value.

SUMMARY OF THE INVENTION

An object of the present invention is to provide a reagent for the determination of serum triglycerides which is useful for a clinical test with lipoprotein lipase-glycerol dehydrogenase.

Another object of the present invention is to provide a method for determining serum triglycerides wherein triglycerides can be determined in one step according to enzymatic reaction and colorimetry can be effected at a wave length in the visible ray region.

According to the present invention, there is provided a combination of reagents consisting essentially of (1) enzymes, i.e., lipoprotein lipase, glycerol dehydrogenase and coenzyme NAD and (2) an aqueous solution of a mixture of a tetrazolium compound and phenazine methosulfate.

BRIEF EXPLANATION OF THE DRAWING:

FIG. 1 shows close correlation between the conventional acetylacetone method and the method of the present invention for triolein analysis.

DETAILED DESCRIPTION OF THE INVENTION:

Mechanism of the enzymatic reaction according to the reagent of the present invention can be illustrated as follows;

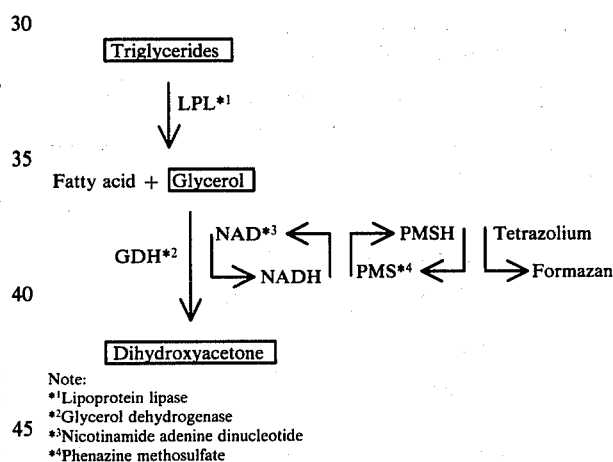

Note:
*[1]Lipoprotein lipase
*[2]Glycerol dehydrogenase
*[3]Nicotinamide adenine dinucleotide
*[4]Phenazine methosulfate In the above enzymatic reactions, the reaction of hydrolyzing triglycerides into fatty acid and glycerol by the action of enzyme LPL proceeds in the direction of the arrow, while the dehydrogenation reaction of thus formed glycerol to form dihydroxyacetone by the action of GDH in the presence of coenzyme NAD has an equilibrium which is inclined in the formation of NAD. According to the present invention, the dehydrogenation reaction of glycerol can be forced to proceed in the direction of the arrow by adding previously PMS and a tetrazolium compound in addition to coenzyme NAD to the reaction reagent. Therefore, the hydrolysis reaction of triglyceride and dehydrogenation reaction of glycerol with the enzymes are performed in one step and, at the same time, a color developed by the reaction of reducing the tetrazolium compound into formazan is determined colorimetrically at a wave length in visible ray region, thereby determining an amount of the triglyceride.

As illustrated above, NADH formed quantitatively from the triglyceride reduces the tetrazolium compound quantitatively into formazan through a step of converting PMS into PMSH. Degree of color development of the reaction liquid in visible ray region is proportional to the amount of the triglyceride and, therefore, the determination of the triglyceride as above is possible.

The reactions caused by the reagent of the present invention are carried out usually at a temperature of, for example, 37° C for 20 minutes and then, pH of the reaction mixture is reduced by the addition of a 0.1 N HCL solution to terminate the reaction.

LPL may be obtained from a culture liquid of chromobacterium viscosum var. paralipolyticum. GDH may be obtained from a culture liquid of bacillus megatherium.

The enzyme-coenzyme reagent of the present invention is prepared preferably by dissolving LPL, GDH and NAD in a buffer solution and freeze-drying the solution. The buffer solution is not particularly limited except that the solution should exhibit the buffer action in the pH range of 7.0–9.5. Preferred buffer solution is a 0.1 M phosphate buffer solution (pH 7.6). The buffer solution may be added to the mixture of tetrazolium compound and PMS instead of the enzyme-coenzyme reagent.

PMS which has been considered to be very unstable can be kept stably for a long period of time by preserving it in the form of an aqueous solution of a mixture thereof with a tetrazolium compound in a brown polyethylene reagent bottle at a cold dark place.

The present invention will be described in more detail by way of a non-limitative example.

In the Example, one unit of GDH is indicated by a quantity of GDH capable of isolating one micromol NADH at 25° C for one minute with use of glycerol as a substrate and coenzyme NAD, and one unit of LPL is indicated by 2.5 times the international unit measured according to the PVA emulsion method.

EXAMPLE

I. Formulation of reagents:

1. The first vial (enzyme-coenzyme reagent):

| LPL | 20,000 units |
|-----|--------------|
| GDH | 1,000 units |
| NAD | 500 mg |

The above composition is dissolved in 100 ml. of a 0.1 M phosphate buffer solution (pH 7.6) and 5.0 ml. aliquots of the solution are freeze-dried.

2. The second vial:

| Nitrotetrazolium Blue | 50 mg |
|-----------------------|-------|
| Phenazine methosulfate | 10 mg |

Purified water is added to the above components to make the total quantity 100 ml.

II. Procedure:

The content (5.0 ml) of above enzyme-coenzyme vial (1) is dissolved in 5.0 ml. of the content of vial (2) to obtain the reaction solution. 0.5 ml. of the reaction solution (containing 100 units of LPL and 50 units of GDH) is placed in a test tube and added with 0.02 ml. of a serum sample. The reaction is carried out at 37° C for accurately 20 minutes. Directly thereafter, the reaction is terminated by adding 5.0 ml. of a 0.1 N HCl solution thereto to reduce a pH. 5–90 minutes after the termination of the reaction, colorimetric determination is effected in a usual manner at a wave length of 570–600 nm with reference to the reagent blank as control. Separately, the same procedure is repeated by using a standard (freeze-dried serum containing a predetermined amount of triglyceride) to obtain a calibration curve. From the result of the determination, quantity of triglyceride in the sample is calculated.

The reaction time must be controlled strictly, while concentration of the reagents, reaction temperature and pH may be changed unless they influence the determination result.

Results of the analysis of triolein according to the above example are shown in Table 1. Serum samples in the table are prepared by subjecting bloods of respective individual persons to centrifugation in the usual manner.

Table 1

| Serum No. | Triolein mg/dl. | |
|-----------|-----------------|--|
| | Acetylacetone method | Method of the present invention |
| 1 | 1,040 | 1,090 |
| 2 | 990 | 975 |
| 3 | 735 | 735 |
| 4 | 505 | 525 |
| 5 | 463 | 445 |
| 6 | 340 | 340 |
| 7 | 290 | 260 |
| 8 | 190 | 203 |
| 9 | 106 | 110 |
| 10 | 70 | 73 |

Triolein analysis was effected by using 70 samples according to the method of present invention as illustrated in the above example as well as the conventional acetylacetone method. A good close correlation was observed as shown in FIG. 1.

As described above clearly, the reagent of the present invention is a novel one with which triglycerides are determined by a special reaction mechanism. The reagent having advantages which will be described below exhibits a great technical progress in that usual clinical tests are facilitated by the reagent for determination of triglycerides.

The advantages of the reagent of this invention are as follows:

Even a very small quantity of sample can be determined in one step; lipoprotein-combinative triglycerides can be determined without being influenced by other components of the blood; another additive such as hydrazine for advancing the reaction is not required; the determination can be effected at a wave length in visible ray region; and no serum blank is required. Thus, the determination does not take a long time, the operation is simple and a device used for the colorimetry is simple.

What we claim is:

1. A method of determining serum triglycerides by hydrolysis according to an enzymatic reaction, wherein a serum is added to a reaction liquid obtained by adding an aqueous solution of a mixture of a tetrazolium compound and phenazine methosulfate to an enzyme-coenzyme reagent comprising lipoprotein lipase (LPL), glycerol dehydrogenase (GDH) obtained from bacillus megatherium and nicotinamide adenine dinucleotide (NAD), thereby effecting an enzymatic hydrolysis of the triglycerides and dehydrogenation of the resulting glycerol in one step with simultaneous reduction of the tetrazolium compound to formazan and determining colorimetrically at a wavelength in the range of 570–600nm the color developed by said reduction.

2. A method of determining serum triglycerides according to claim 1, wherein LPL is an enzyme obtained from a culture liquid of chromobacterium viscosum var. paralipolyticum.

* * * * *

UNITED STATES PATENT AND TRADEMARK OFFICE
CERTIFICATE OF CORRECTION

PATENT NO. : 4,038,146
DATED : July 26, 1977
INVENTOR(S) : Urao NONAKA et al

It is certified that error appears in the above-identified patent and that said Letters Patent are hereby corrected as shown below:

IN THE HEADING:

The name of the Assignee should read:

-- Assignee: Iatron Laboratories, Inc.

Signed and Sealed this

First Day of November 1977

[SEAL]

Attest:

RUTH C. MASON
*Attesting Officer*

LUTRELLE F. PARKER
*Acting Commissioner of Patents and Trademarks*